(12) United States Patent
Grant et al.

(10) Patent No.: US 8,500,054 B2
(45) Date of Patent: Aug. 6, 2013

(54) INFUSION SET IMPROVEMENTS

(75) Inventors: Kevin L. Grant, Litchfield, NH (US);
Larry B. Gray, Merrimack, NH (US);
Matthew C. Harris, Bow, NH (US);
Jeffrey L. Klein, Manchester, NH (US);
Craig R. Steinfels, Manchester, NH (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 986 days.

(21) Appl. No.: 11/235,843

(22) Filed: Sep. 27, 2005

(65) Prior Publication Data
US 2006/0065772 A1 Mar. 30, 2006

Related U.S. Application Data

(60) Provisional application No. 60/613,556, filed on Sep. 27, 2004.

(51) Int. Cl.
*B65H 75/38* (2006.01)

(52) U.S. Cl.
USPC ............ 242/388.1; 242/129.2; 242/166; 242/171; 242/272; 242/273; 242/274; 242/346.1; 242/362.1; 242/388; 242/475; 242/476.9; 242/480.5; 242/480.8; 242/370; 242/404; 254/271; 604/153

(58) Field of Classification Search
USPC ........... 242/129.2, 166, 171, 272–274, 346.1, 242/362.1, 388, 475, 476.9, 480.5, 480.8, 242/370, 404, 388.1; 254/271; 604/153
See application file for complete search history.

(56) References Cited

U.S. PATENT DOCUMENTS

| 2,837,292 | A | * | 6/1958 | Adamson | 242/372 |
| 3,420,461 | A | * | 1/1969 | Cousino | 242/326.4 |
| 3,578,255 | A | * | 5/1971 | Gordon et al. | 242/570 |
| 3,730,187 | A | * | 5/1973 | Reynolds | 604/178 |
| 3,809,331 | A | * | 5/1974 | Gaul | 242/388.1 |
| 4,174,816 | A | * | 11/1979 | Olson | 242/272 |

(Continued)

FOREIGN PATENT DOCUMENTS

| JP | 2000/177934 | 10/2000 |
| WO | WO 2004/020023 | 3/2004 |
| WO | WO 2004/020035 | 3/2004 |
| WO | WO 2004/020036 | 3/2004 |

OTHER PUBLICATIONS

International Search Report dated Feb. 22, 2006.
International Search Report, May 19, 2006.

(Continued)

*Primary Examiner* — Nicholas Lucchesi
*Assistant Examiner* — Scott Medway
(74) *Attorney, Agent, or Firm* — McCormick, Paulding & Huber LLP

(57) ABSTRACT

A method and device for adjusting the unstored length of tubing directed to improving the use of infusion sets that deliver fluids to a user. The device includes a storage module and other features for adjusting, storing and securing the length of the tubing. The method of adjusting the length of the tubing to a desired length typically comprises removably attaching the tubing to the adjuster, adjusting the tubing by wrapping the tubing around a hub or post of the adjuster, and fixing the length of the unstored tubing by attaching the tubing to a securing device such as a friction structure or fastener.

11 Claims, 20 Drawing Sheets

U.S. PATENT DOCUMENTS

| | | | | |
|---|---|---|---|---|
| 4,570,866 A * | 2/1986 | Drower | ............... | 242/371 |
| 4,735,371 A * | 4/1988 | Park | ............... | 242/388.9 |
| 4,802,638 A * | 2/1989 | Burger et al. | ............... | 242/388.1 |
| 4,850,974 A * | 7/1989 | Bickelhaupt et al. | ............... | 604/171 |
| 4,913,369 A * | 4/1990 | Lia et al. | ............... | 242/405.2 |
| 5,102,061 A * | 4/1992 | Suzuki et al. | ............... | 242/370 |
| 5,265,822 A * | 11/1993 | Shober et al. | ............... | 242/388.2 |
| 5,279,473 A * | 1/1994 | Rozon | ............... | 242/377 |
| 5,328,112 A * | 7/1994 | Obata | ............... | 242/388 |
| 5,630,456 A * | 5/1997 | Hugo et al. | ............... | 160/173 R |
| 5,637,005 A * | 6/1997 | Bannai et al. | ............... | 439/164 |
| 5,643,214 A | 7/1997 | Marshall et al. | ............... | 604/134 |
| 5,665,071 A | 9/1997 | Wyrick | ............... | 604/134 |
| 5,762,281 A * | 6/1998 | Foley | ............... | 242/376 |
| 5,851,197 A | 12/1998 | Marano et al. | ............... | 604/135 |
| 5,882,216 A * | 3/1999 | Matsumoto et al. | ............... | 439/164 |
| 5,984,224 A * | 11/1999 | Yang | ............... | 242/400.1 |
| 6,086,008 A * | 7/2000 | Gray et al. | ............... | 242/388.6 |
| 6,093,172 A | 7/2000 | Funderburk et al. | ............... | 604/135 |
| 6,179,238 B1 * | 1/2001 | Phillipps | ............... | 242/378.4 |
| 6,213,797 B1 * | 4/2001 | Best et al. | ............... | 439/164 |
| 6,234,418 B1 * | 5/2001 | Donaldson | ............... | 242/402 |
| 6,293,925 B1 | 9/2001 | Safabash et al. | ............... | 604/136 |
| 6,302,716 B1 * | 10/2001 | Matsumoto et al. | ............... | 439/164 |
| 6,354,854 B1 * | 3/2002 | Matsuzaki | ............... | 439/164 |
| 6,434,249 B1 * | 8/2002 | Wei | ............... | 381/370 |
| 6,446,898 B1 * | 9/2002 | Hwang | ............... | 242/378.1 |
| 6,582,403 B1 | 6/2003 | Bierman et al. | ............... | 604/174 |
| 6,719,238 B1 * | 4/2004 | Grant et al. | ............... | 242/548.4 |
| 7,216,665 B1 * | 5/2007 | Sims, Jr. | ............... | 137/355.19 |
| 7,229,042 B2 * | 6/2007 | Thebault et al. | ............... | 242/388.1 |
| 7,654,484 B2 * | 2/2010 | Mogensen et al. | ............... | 242/402 |
| 7,922,711 B2 * | 4/2011 | Ranalletta et al. | ............... | 604/539 |
| 2003/0122021 A1 * | 7/2003 | McConnell et al. | ............... | 242/388.1 |
| 2003/0122023 A1 * | 7/2003 | Pitcher | ............... | 242/388.1 |
| 2003/0141407 A1 * | 7/2003 | Dannecker et al. | ............... | 242/588 |
| 2006/0011763 A1 * | 1/2006 | Kuo | ............... | 242/378.1 |
| 2006/0186256 A1 * | 8/2006 | Mogensen et al. | ............... | 242/405.1 |

OTHER PUBLICATIONS

Tubeguard, Intra Pump Infusion Systems, Grapevine, TX, 2 pgs.

* cited by examiner

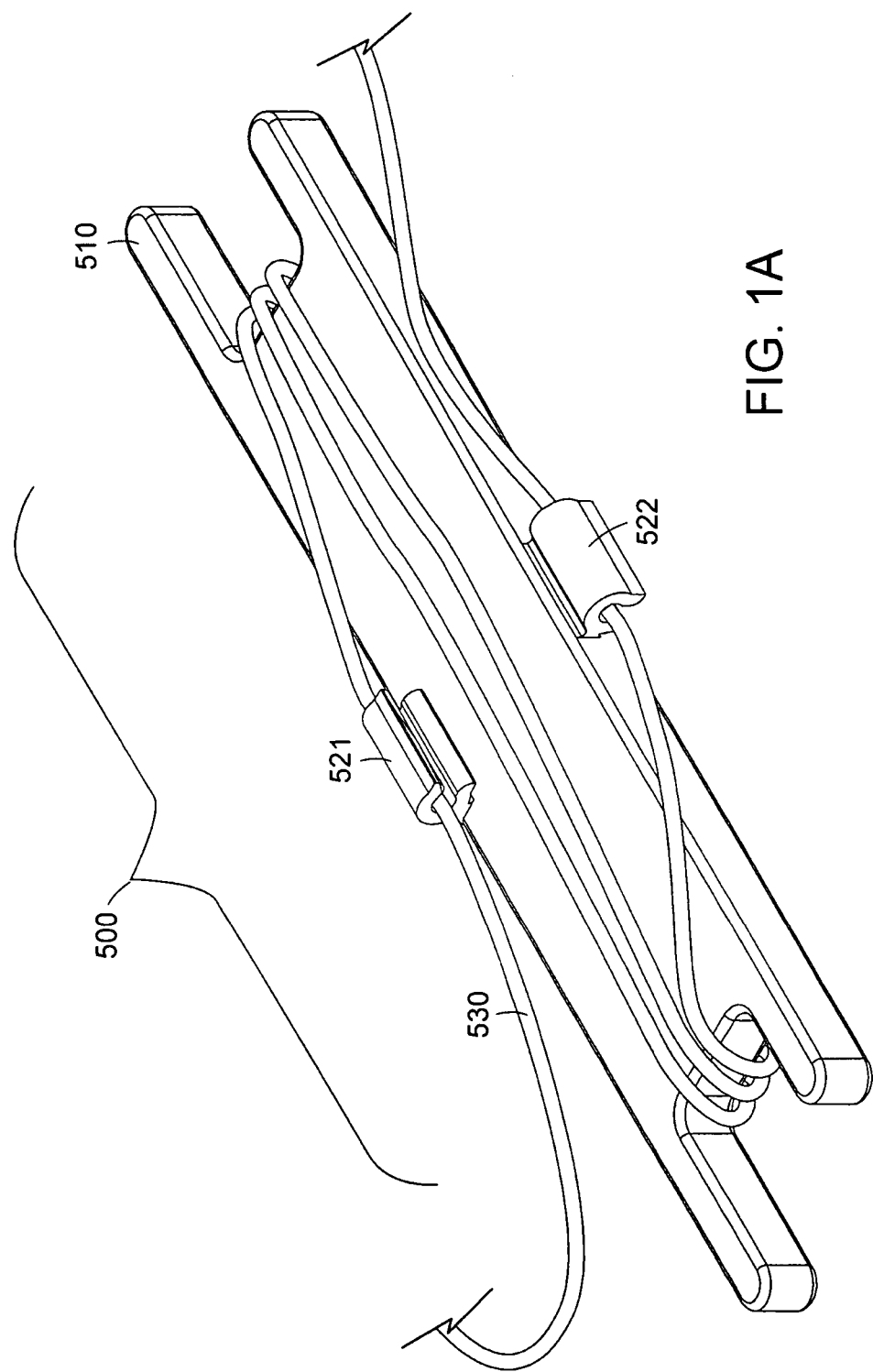

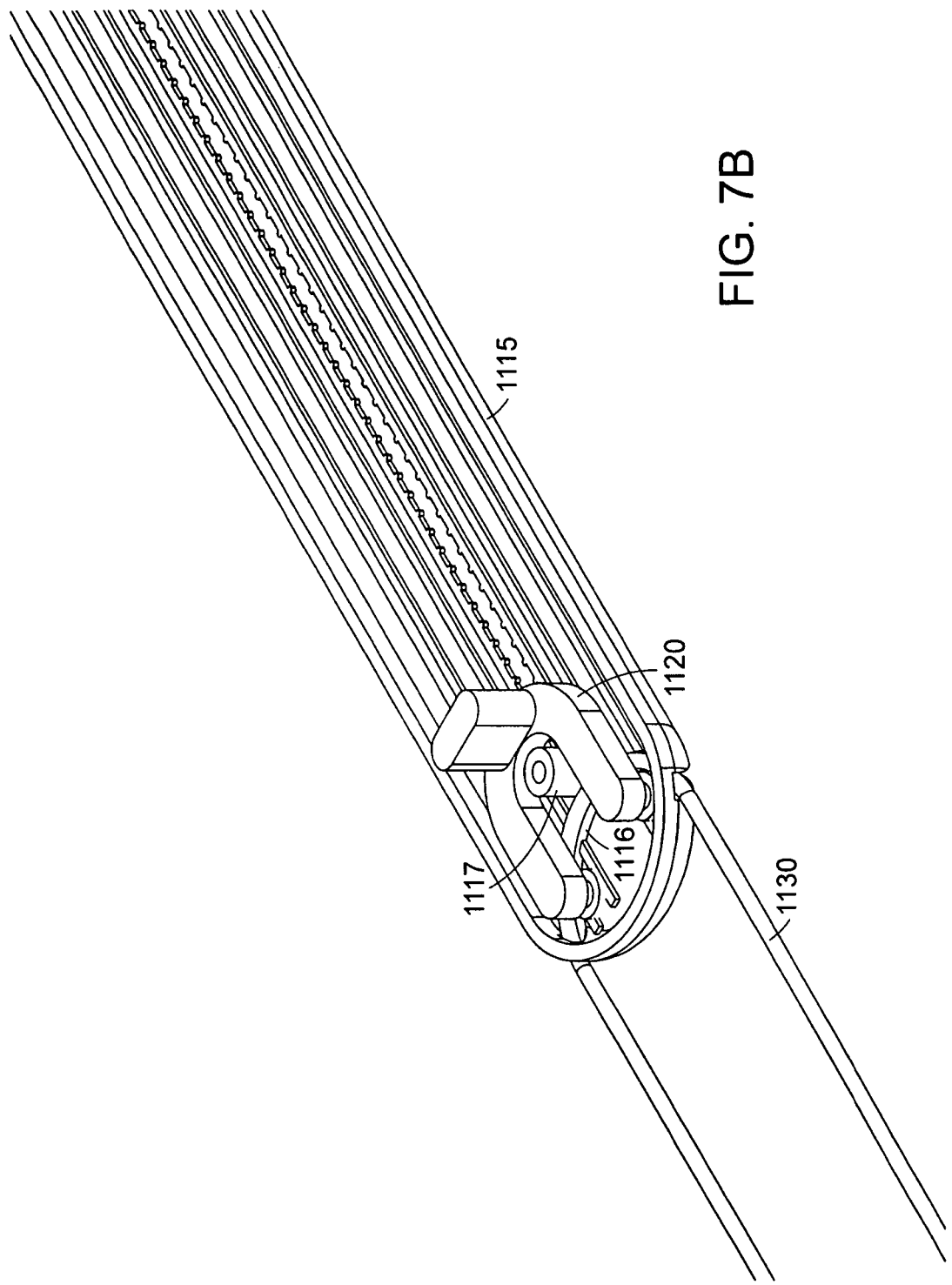

INFUSION SET IMPROVEMENTS

CROSS REFERENCE TO RELATED APPLICATIONS

This application claims priority from U.S. provisional patent application Ser. No. 60/613,556, entitled "Infusion Set Improvements," filed Sep. 27, 2004, which is hereby incorporated by reference, in its entirety.

TECHNICAL FIELD

The present invention relates to methods and objects directed to improving the use of infusion sets to deliver fluids to a patient, for example the delivery of insulin to a patient suffering from diabetes. More particularly, the invention relates to methods and objects of adjusting the length of tubing used in an infusion set.

BACKGROUND ART

Infusion sets are typically used to transfer fluids from a source to a patient. An infusion set typically includes a cannula assembly that may be made up of a cannula which is inserted into a patient with the use of a needle, and a cannula body which is used to hold the upstream end of the cannula. The needle is typically removed before fluid may be transferred through the cannula. The cannula body may be used to secure the cannula to a patient's body in a specific position. The cannula is attached to a tube, usually a flexible tube, which conducts fluid from a source to be transferred to the body.

Infusion sets may present a number of user-oriented, operational problems due to the competing interests of providing a device capable of being used by many, while being tailored to an individual's needs.

In one aspect of infusion sets, the length of a tube used in an infusion set must be able to reach a distance between the insertion site of the cannula and the source of the infused fluid. The tubes are typically flexible, allowing for convenience in handling by users. In the instance when a source is a portable source that may be worn by a patient, the length of tube necessary depends upon the relative positions of the source and the insertion site, which may be a function of the size of the patient. As well, patients may wish to alter the position where they wear the source and/or the insertion site depending upon individual circumstances. Tube suppliers manufacture various lengths of tubes. However, requiring patients to purchase various lengths of tubing depending upon their needs, and requiring suppliers to stock every length of tubing desired may be impractical. Patients who use tubes that are too long may insure that an adequate length is available, but risk entangling the excess tube in stray objects or potentially dislodging the cannula assembly or fluid source if the excess tubing snags.

In general, a need exists to improve the design of infusion sets to address this problem.

SUMMARY OF THE INVENTION

Embodiments of the invention utilizing a tube length adjuster may be directed toward adjusting an unstored length of a tube used to carry fluids from a source to a patient. The adjuster may be capable of storing a portion of tubing within its structure, and leaving an unstored length of exposed tubing. Thus, the effective length of tubing connecting a source and an insertion point, using some embodiments of the invention, is approximately the length of unstored tubing plus some length defined by the physical dimension of the adjuster. The adjuster may allow a user to adjust the length of unstored tubing depending upon the needs of the user.

A tube length adjuster, according to embodiments of the invention, includes a storage module for storing a portion of excess tubing length, relative to the desired effective tube length. Such an adjuster may be utilized in a method of adjusting an unstored length of tubing used to transfer fluid to a living body according to another embodiment of the invention. The method includes the steps of providing an adjuster; providing a tube for transferring at least some fluid; removably attaching the tube to the adjuster; and storing a portion of the tube on the storage module to adjust the unstored length of tube. Alternatively, the method may include the step of fixing the unstored length of the tube.

In accordance with embodiments of the invention an adjuster is provided for adjusting the unstored length of tubing used to transfer at least some fluids from a source to a user. Preferably, the user wraps the unstored tubing around the storage module until the user achieves the desired length. Additionally, the adjuster may include features to maintain the length of stored tubing around the adjuster and/or enable the secure attachment or placement of the adjuster.

In accordance with other embodiments of the present invention, a user may attach the tubing to the adjuster and rotates, winds, spins or stores the tubing inside the storage module. The user may then fix the length of the unstored tubing by securing the tubing and/or closing the storage module. Furthermore, the storage module may have friction structures incorporated into the housing to secure the tubing. To unsecure the tubing the user disengages the tubing from the friction structure.

In accordance with yet other embodiments of the invention, the tubing may be retractably guided into the storage module. Similarly, the user may fix the length of the unstored tubing by securing the tubing, engaging a friction structure, or closing the storage module. When a different length of tubing is required, a tug on the tubing can retract the tubing from the storage module.

Some embodiments of the invention are directed toward improvements in the use of infusion sets for injecting fluids into patients. Such infusion sets are typically designed for injecting fluids into human beings, but can also be utilized in conjunction with other mammals, animals, and other living beings. The embodiments of the invention directed to adjusting the unstored length of a tube are not restricted to tubing of a particular length or diameter. In addition, the embodiments of the invention are not necessarily restricted to uses of adjusting the length of tubing used to transfer fluids to patients. Some embodiments of the invention may be utilized in other applications in which adjusting the length of flexible tubing is advantageous.

As is readily apparent to those skilled in the art, a variety of different arrangements of different structures, including arrangements not mentioned herein, may be utilized to create adjusters capable of being used with the method described above.

BRIEF DESCRIPTION OF THE DRAWINGS

The foregoing features of the invention will be more readily understood by reference to the following detailed description, taken with reference to the accompanying drawings, in which:

FIG. 1A schematically shows a tube length adjuster, in accordance with an embodiment of the present invention;

FIG. 4B schematically shows a top view of the tube length adjuster shown in FIG. 4A;

FIG. 7A-7D show an exploded view and the mechanism of a tube length adjuster having a variable internal path for holding tubing, in accordance with an embodiment of the present invention;

DETAILED DESCRIPTION OF SPECIFIC EMBODIMENTS

Figure 1B:
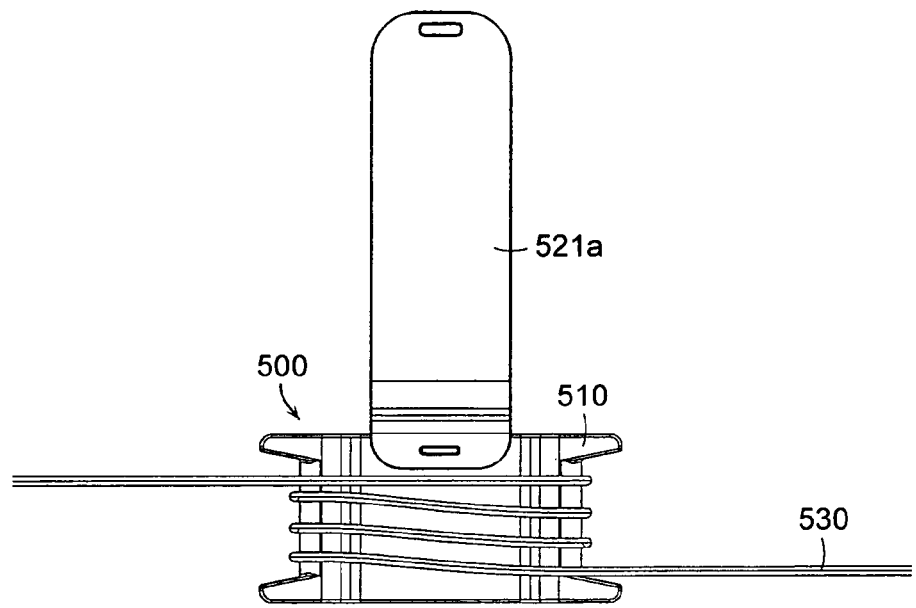
FIG. 1B schematically shows a tube length adjuster having a fastener, in accordance with an embodiment of the invention.
Figure 1C:
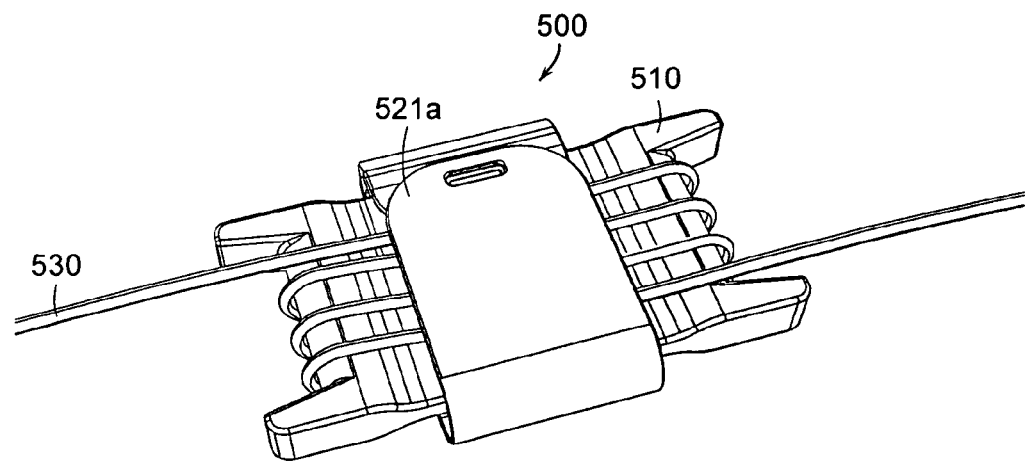
FIG. 1C schematically shows the tube length adjuster of FIG. 1B with the fastener wrapped around the tubing.

FIGS. 1A-1C show various embodiments of a tube length adjuster, all of which are in accord with embodiments of the invention. The adjuster 500 includes a storage module 510 for storing excess tube length by wrapping the tube 530 around the module 510, and a fastening device such as friction structures 521, 522 for maintaining the length of stored tubing around the adjuster 500. Using the embodiment shown in FIG. 1A, the tubing 530 is removably attached to the adjuster using one of the friction structures 521, 522, and the length of unstored tubing is fixed by attaching the tube 530 to the unused friction structure after a portion of tubing 530 is wrapped around the module 510. In another embodiment of the invention, a fastening device such as a fastener 521A may be attached to the module 510 as shown in FIG. 1B. The fastener 521A may be wrapped around the tubing stored around the module 510, to fix the length of the unstored tubing as shown in FIG. 1C. The fastener 521A may be molded as part of the module 510 to form a unitary unit or separately attached to the module after manufacturing the module. When the adjuster with the fastener is molded as a unitary structure, preferably, the fastener is overmolded after the module is molded. Although two examples of fastening devices are shown, a person of skill in the art will recognize that other fastening devices may be used. Such fasteners, although not shown, are within the scope of the invention.

Figure 2A:
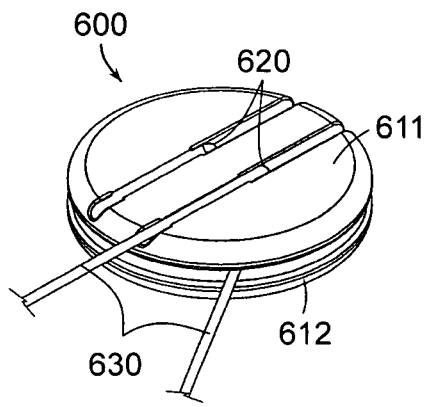
FIGS. 2A-2D illustrate a sequence of attaching tubing to a tube length adjuster, in accordance with an embodiment of the present invention.
Figure 2B:
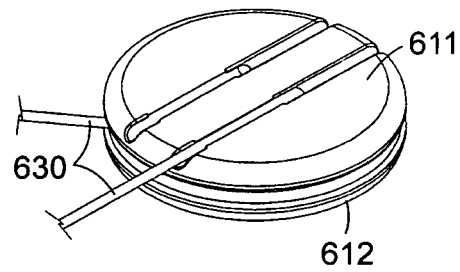
Figure 2C:
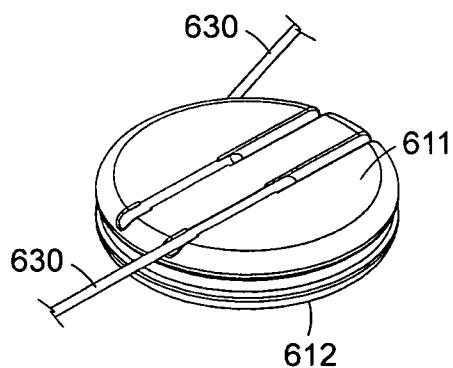
Figure 2D:
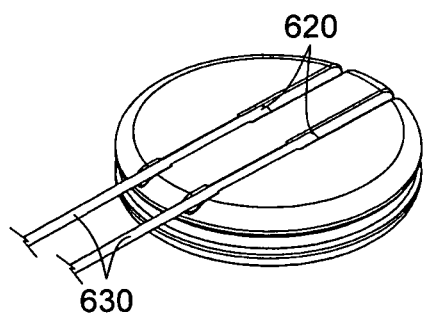

Other types of tube length adjusters may be used in conjunction with the method. Some examples of such adjusters are shown in FIGS. 2-4, all of which are in accord with embodiments of the invention. FIGS. 2A-2D depict an adjuster 600 with a storage module including an inner hub sandwiched between two halves 611, 612. One half has a pair of notches 620 for removably attaching tubing 630. Thus a method of adjusting the length of tubing includes the steps of: removably attaching the tubing 630 in one of the notches 620 (as shown in FIG. 2A); storing the tubing 630 by wrapping the tubing 630 around the hub and between the halves 611, 612 to adjust the unstored tubing to a desired length (as shown in FIGS. 2B and 2C); and fixing the length of the unstored tubing by attaching the tubing 630 in the remaining open notch 620 (as shown in FIG. 2D).

Figure 3A:
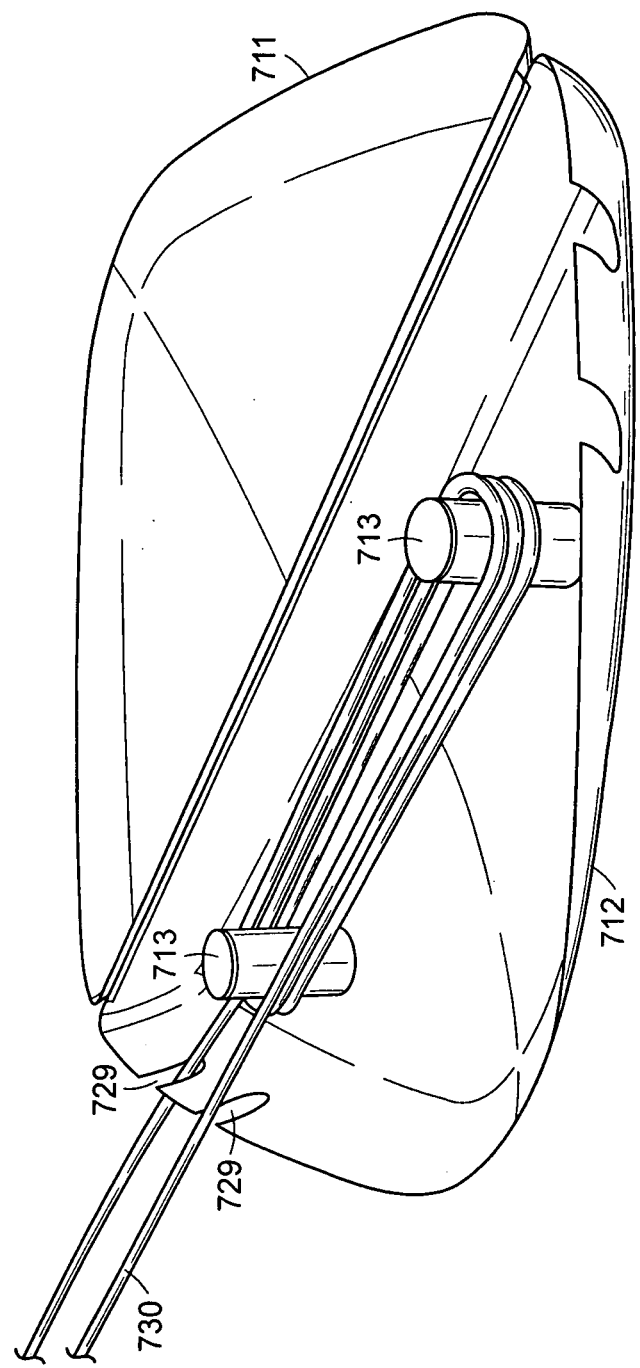
FIGS. 3A-3B schematically show a tube length adjuster having a case that opens, in accordance with an embodiment of the present invention.
Figure 3B:
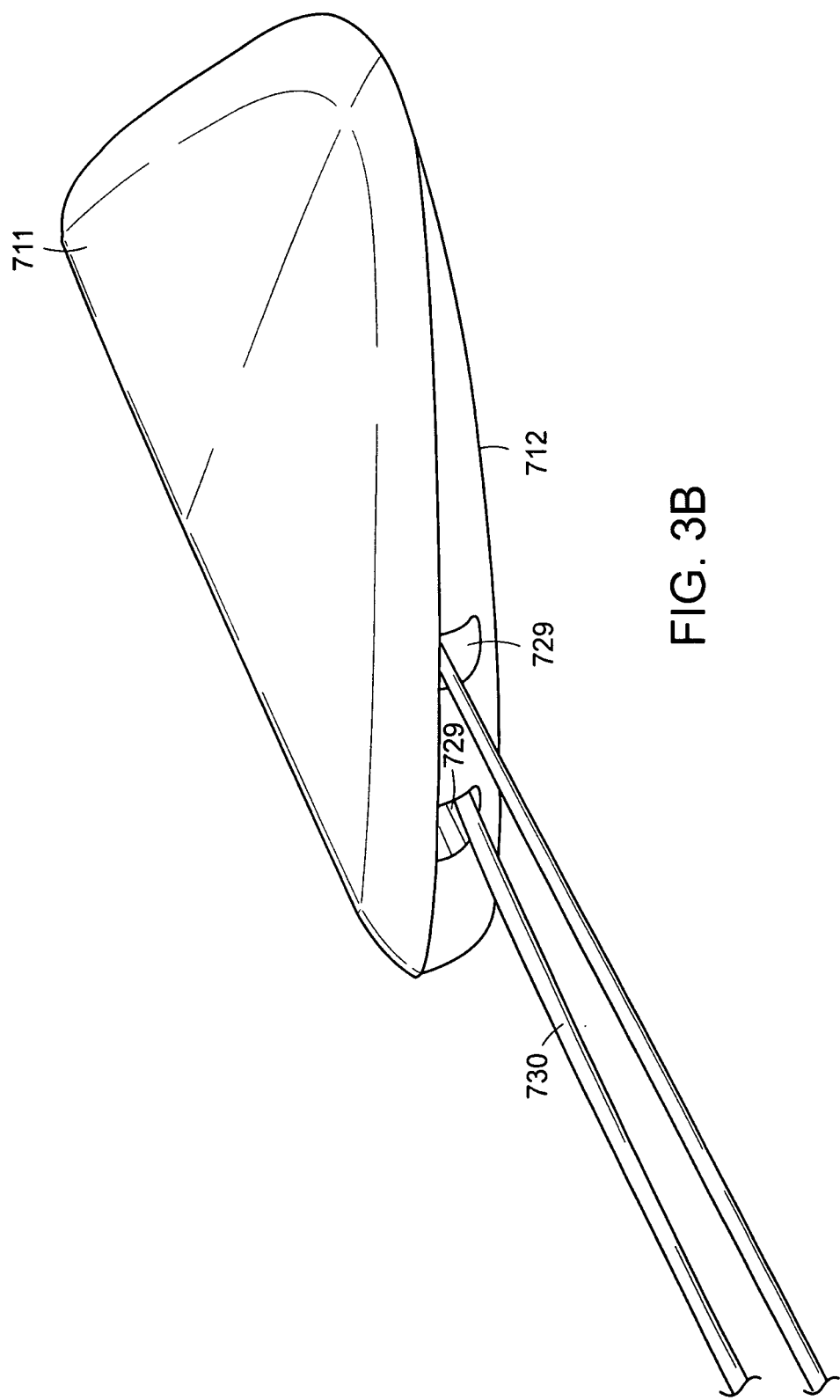

FIGS. 3A and 3B depict another adjuster in accord with the invention. As shown in FIG. 3A, the adjuster includes at least a pair of hubs 713 which are exposed when the adjuster is opened by lifting open a first half 711 of a case of the adjuster from the second half 712. The halves 711, 712 may optionally be attached by a hinge-like structure as shown in FIG. 3A. The hinge-like structure may be any shape. Tubing 730 may be stored by the adjuster by wrapping the tubing 730 about at least a hub 713 to adjust the unstored length. Preferably, the adjuster has a pair of hubs 713 for adjusting the length of the unstored tubing. The first half 711 may be attached to the second half 712 after the wrapping is complete to fix the length of the unstored tubing, as shown in FIG. 3B. As shown in FIGS. 3A and 3B, a pair of openings 729 may be included in the adjuster.

Figure 4A:
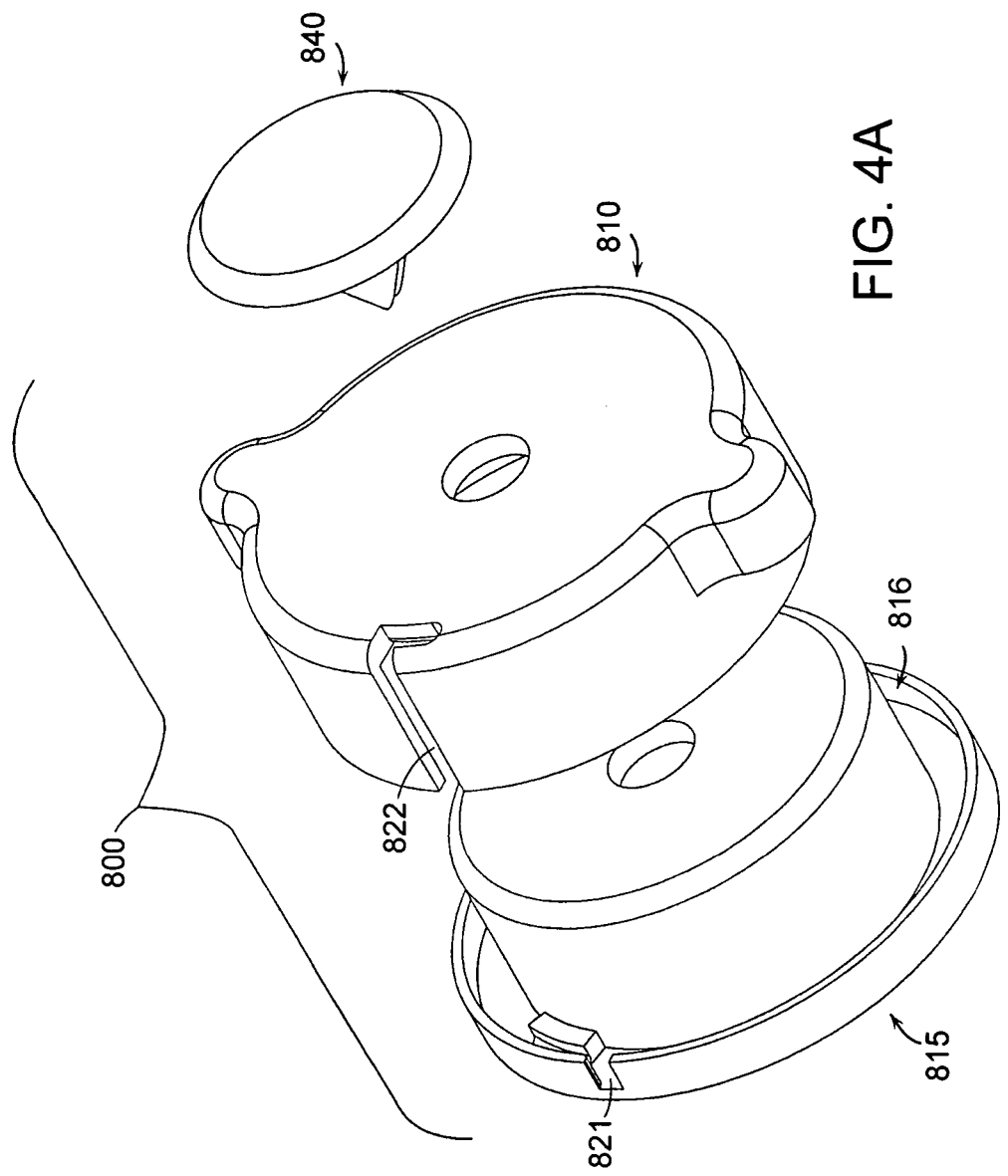
FIGS. 4A-4B schematically show an exploded side of a tube length adjuster, in accordance with an embodiment of the present invention.
Figure 4B:
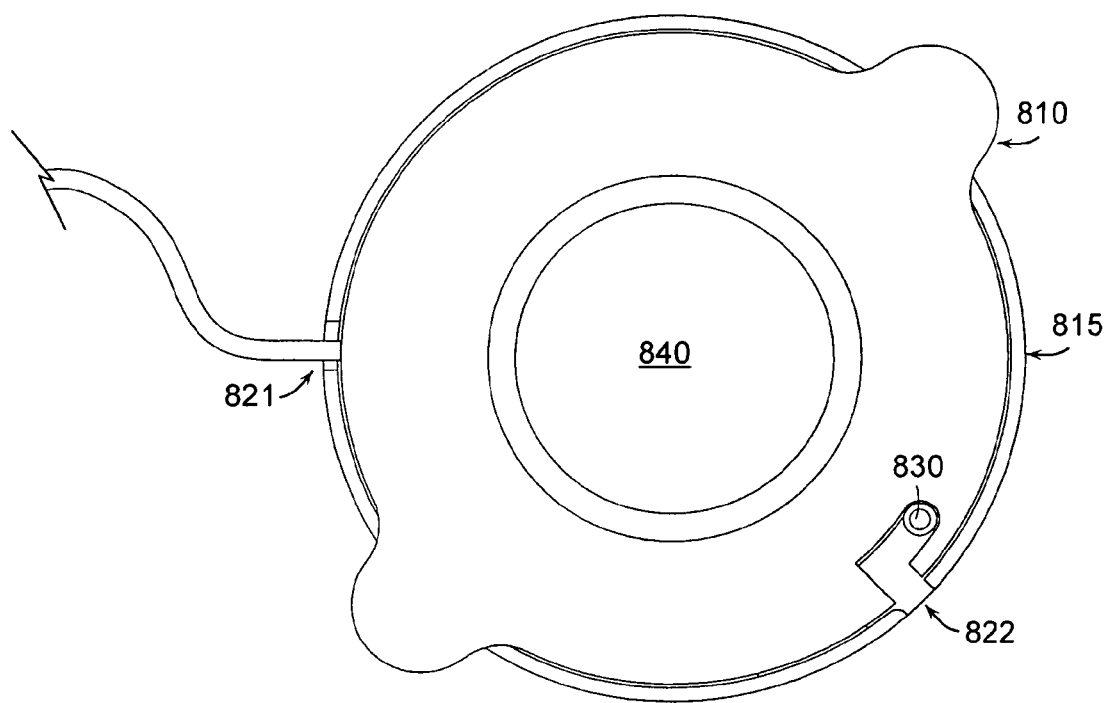

FIGS. 4A and 4B depict another embodiment of the present invention that may be used to adjust the length of unstored tubing. FIG. 4A shows an exploded view of an adjuster 800, which includes the elements of a bottom half, 815 with a circular hub 816 and a friction notch 821 to thread one end of the tube; a top half 810 with a notch-opening 822 for threading the tube out of the adjuster 800, and a cap 840 for locking the positions of the two halves 810, 815 in place. With the two halves 810, 815 separated, the tube may be attached to the bottom notch 821 to removably attach the tube to the adjuster 800. Next, a portion of the tube may be stored by wrapping the tube around the hub 816 to adjust the length of unstored tubing. The top half 810 may then be placed over the bottom half 815, with the loose end of tube threaded through the notch-opening 822. Finally, the cap 840 may be used to lock the halves in place, as shown in FIG. 4B, thus fixing the length of the unstored tubing. An alternative way of adjusting the unstored length of tubing is by rotating the first half 810 while keeping the second half 815 relatively stationary. As described above, the user can thread the tubing through the notch-opening 822 and place the cap 840 to secure it in place, when the desired length is reached.

Figure 5C:
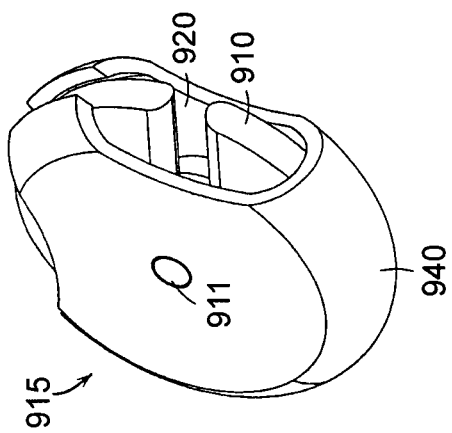
FIG. 5C schematically shows an isometric view of the tube length adjuster shown in FIG. 5A, in accordance with an embodiment of the present invention.
Figure 5B:
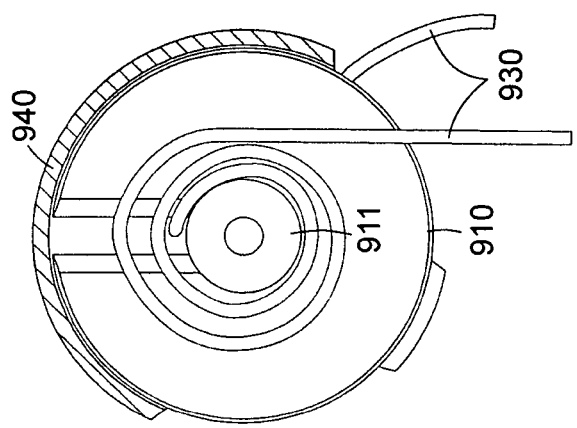
FIG. 5B schematically shows a top view of the tube length adjuster shown in FIG. 5A, in accordance with an embodiment of the present invention.
Figure 5A:
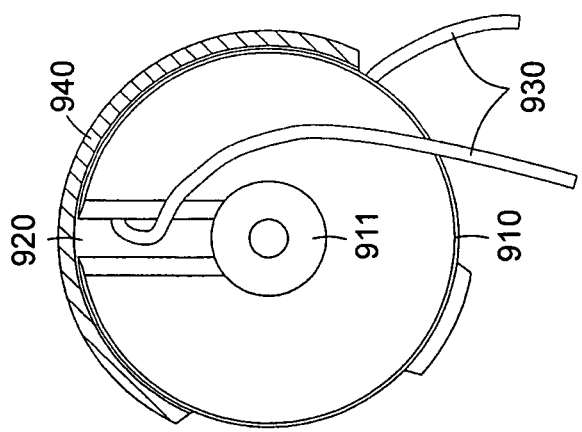
FIG. 5A schematically shows a top view of a tube length adjuster having a rotatable wheel, in accordance with an embodiment of the present invention.

FIGS. 5 and 6 show two other embodiments of adjusters, which may be used to practice the method of adjusting an unstored length of tubing. FIG. 5C depicts a rotatable wheel 910 attached to a body 940, the rotatable wheel 910 acting as the storage module and having a hub 911. As shown in FIG. 5A, the rotatable wheel 910 includes a notch 920 that may act as a entry point for tubing 930 into the adjuster; the notch 920 may also serve to removably attach the tubing 930. The wheel 910 may be rotated to store tubing 930 by wrapping the tubing 930 around the hub 911, and adjusting a length of unwrapped tubing, as shown in FIG. 5B. Rotation of the wheel 910 may be achieved by a handle coupled to the wheel 910 through the body 940 to allow easy rotation by hand. Alternatively, the wheel 910 may be rotated by a spring, preferably a torsional spring, with the spring coupled to the wheel 910 such that the wheel 910 tends to rotate and wrap tubing 930 around the hub 911. When the spring constant of the spring is of sufficient magnitude, the tension in the tubing 930 induced by the spring may be used to fix the length of unstored tubing. The use of a torsional spring may advantageously allow the release of the stored tubing, if an excessive force is applied to the unstored tubing. The release of the stored tubing may relieve the force applied to the unstored tubing. Generally, storing the tubing may also provide additional safety by preventing a cannula assembly from being inadvertently removed from a patient by snagged tubing. Alternatively, a lock mechanism, such as a frictional structure, as described earlier, may be used to fix the length of the unstored tubing in a more secure manner.

Figure 6C:
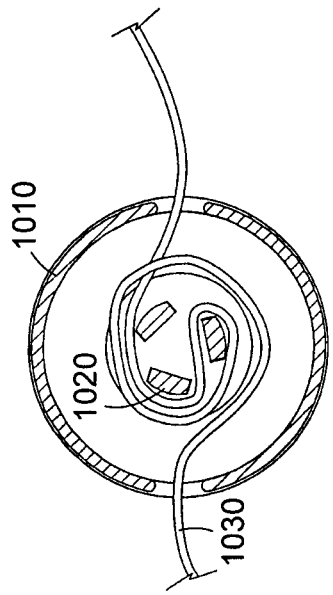
FIGS. 6A-6F illustrate a sequence of attaching tubing to a tube length adjuster for storage, in accordance with an embodiment of the present invention.
Figure 6B:
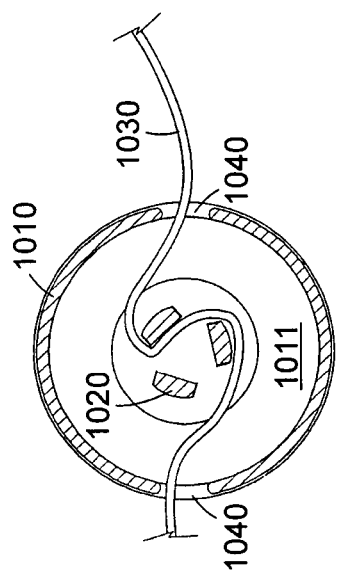
Figure 6A:
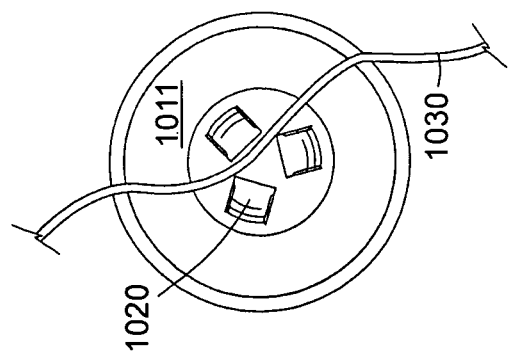
Figure 6F:
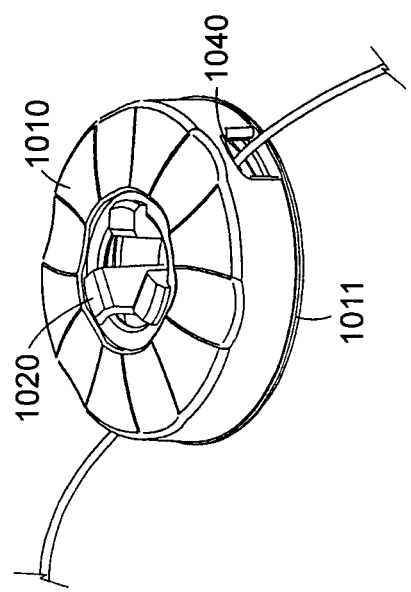
Figure 6E:
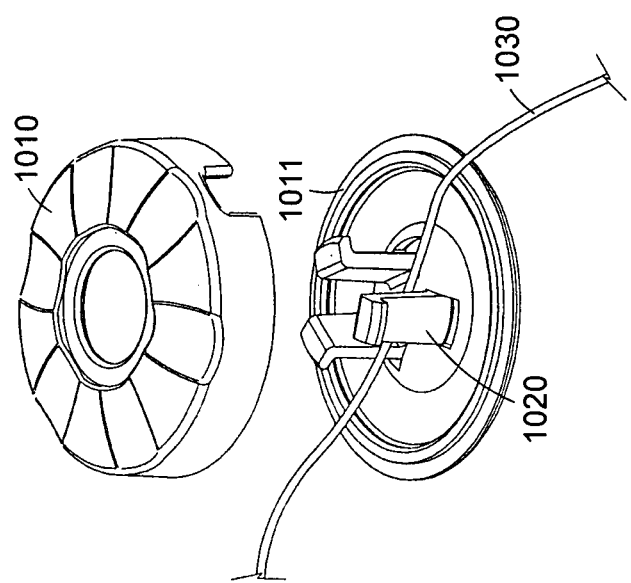
Figure 6D:
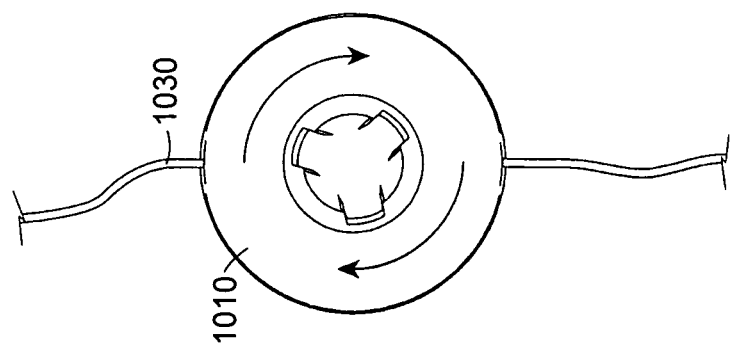

FIGS. 6A-6F depict another adjuster with a rotatable member 1010. The storage module, shown in FIGS. 6A-6F is coupled to the rotatable member 1010 and includes a raised hub structure 1020 for removably attaching a tube 1030 by threading the tube 1030 within the hub structure 1020 as shown in FIG. 6A. The hub structure may include a plurality of posts. Preferably, the hub structure has at least two posts. Rotation of the member 1010 results in two ends of the tubing 1030 simultaneously being wrapped around the hub structure 1020, as depicted in FIGS. 6B and 6C. The storage module is enclosed in a case made of two halves 1010, 1011, one half 1010 being the rotatable member coupled to the storage module and the other half with the raised hub structures. The halves 1010, 1011 may be separated while the tubing 1030 is removably attached to the hub structure 1020, and coupled when tube storage occurs, as shown in FIGS. 6D and 6F. Rotation of the rotatable members 1010 or 1011 stores a portion of the tubing by wrapping the tubing around the storage module. Rotation of the member 1010 or 1011 may be performed manually, such as by hand or automatically, by using a spring such as a torsional spring, as described in the description of the embodiment shown in FIG. 5. In an embodiment with manual rotation, a handle may be coupled to or molded as part of the rotatable member 1010 or 1011. The halves 1010, 1011 may have at least an opening 1040 for tubing 1030 to enter and exit the casing. Preferably, the halves have a pair of openings as shown in FIG. 6B.

In another embodiment of the invention shown in FIGS. 7-10, a tube length adjuster is presented with a variable internal path for holding tubing. An exploded view of one example of such an adjuster is shown in FIGS. 7A-7D. The adjuster shown in FIG. 7A includes a case and a storage module. The case has two halves 1110, 1115, one half having an opening 1116 for allowing tubing to enter and exit the case. The storage module includes a slider 1120 for moving within two tracks 1122. The slider includes two rollers 1121 for aiding movement of the slider 1120 and tubing within the case.

Figure 7A:
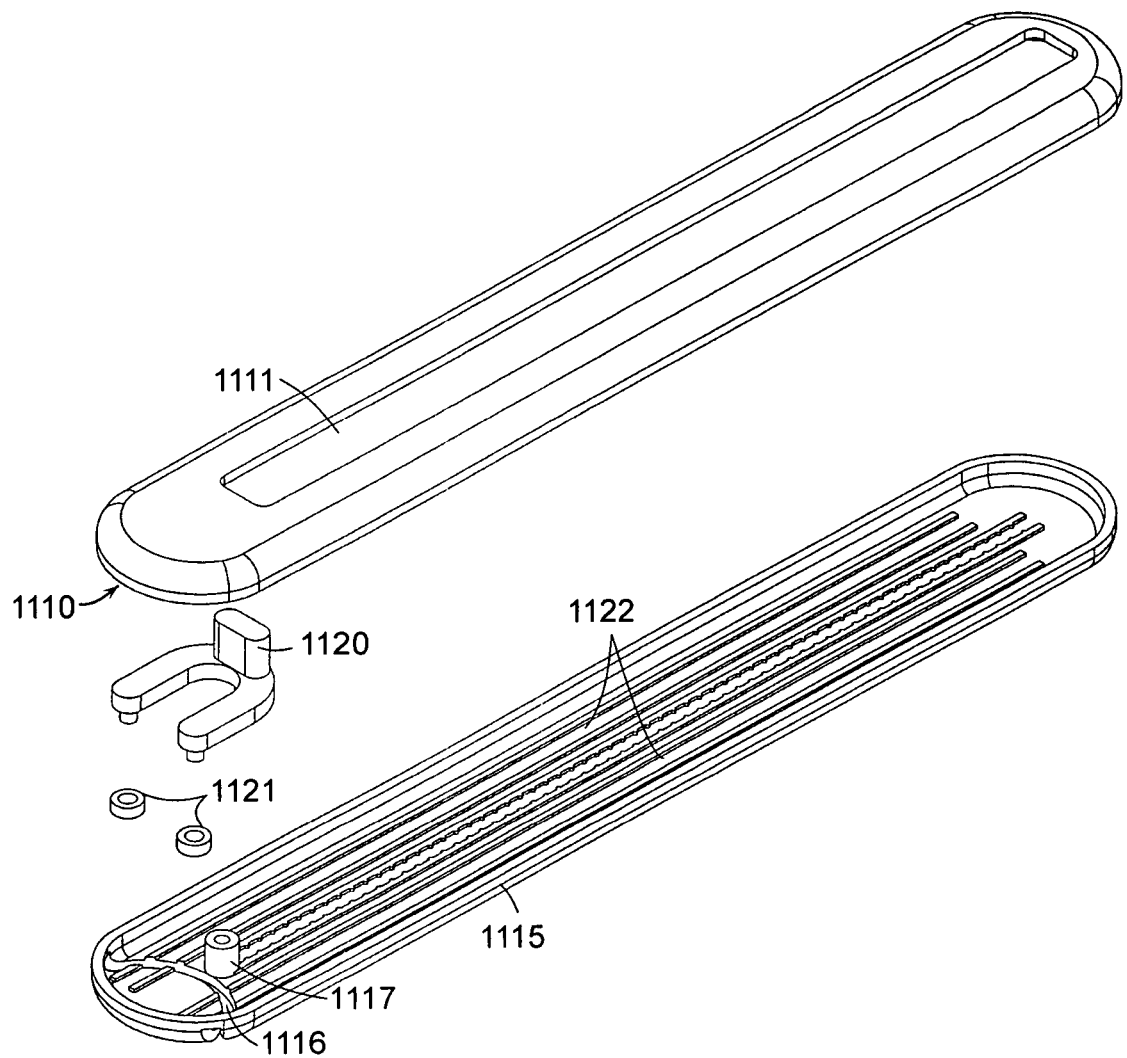
Figure 7C:
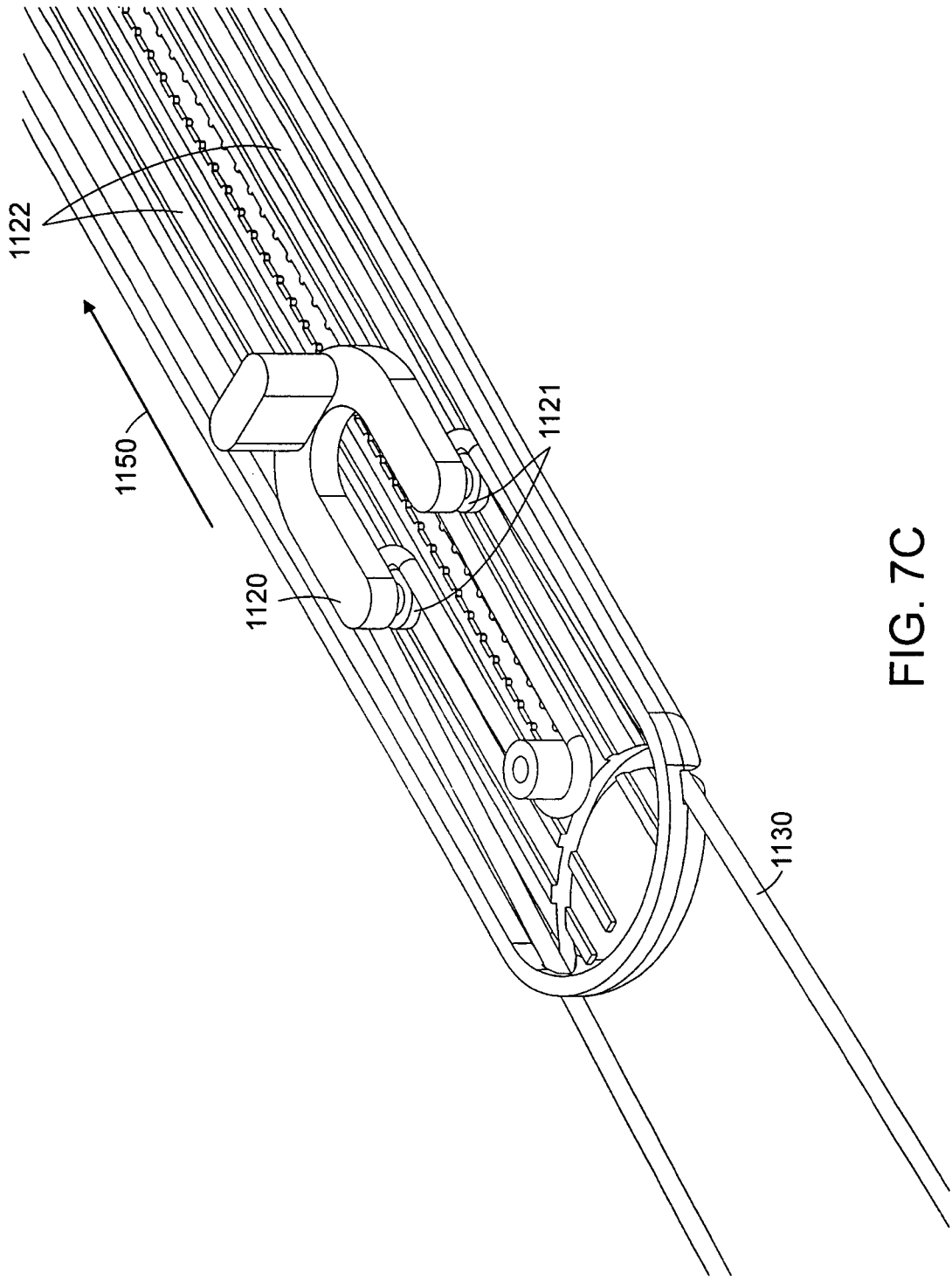
Figure 7D:
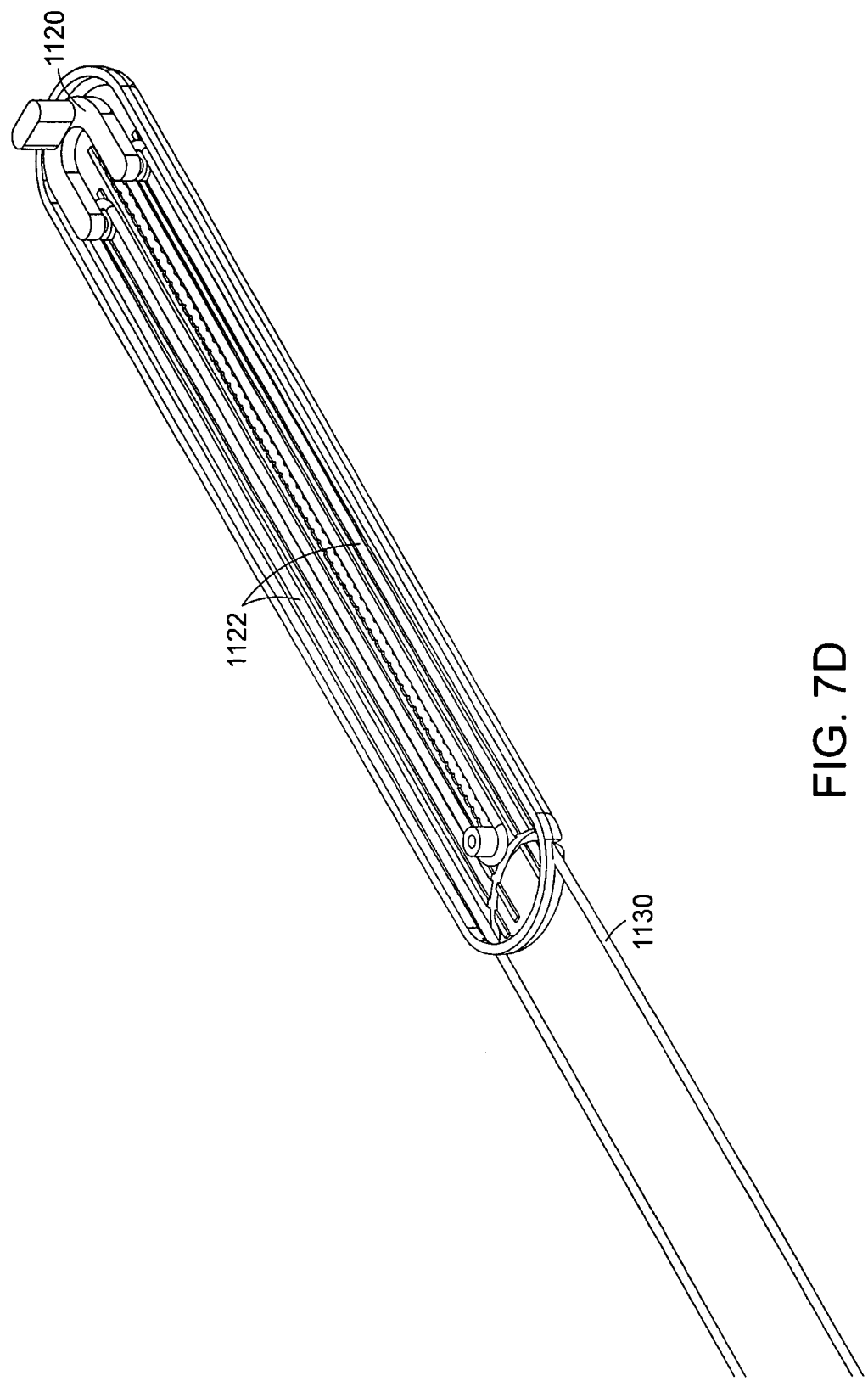

As shown in FIG. 7B, the tubing 1130 is inserted into the case through the opening 1116, and secured within the case by the slider 1120 and a guide 1117 coupled to the case bottom 1115. The position of the slider 1120 and guide 1117 define a path for tubing within the case. As shown in FIG. 7C, as the slider 1120 is moved along the tracks 1122 in the direction 1150, the tubing path length within the case changes, allowing for more tubing 1130 to be stored in the case. The rollers 1121 allow tubing 1130 to move in and out of the case, depending upon the position of the slider 1120, as shown in FIGS. 7C and 7D. Now referring to FIGS. 7A and 7D, the top cover 1110 has a slot 1111 for allowing user access to the slider 1120 to move the slider 1120 within the tracks 1122 as shown in FIG. 7D. A locking mechanism may be included to fix the length of tubing taken up within the case.

Figure 8A:
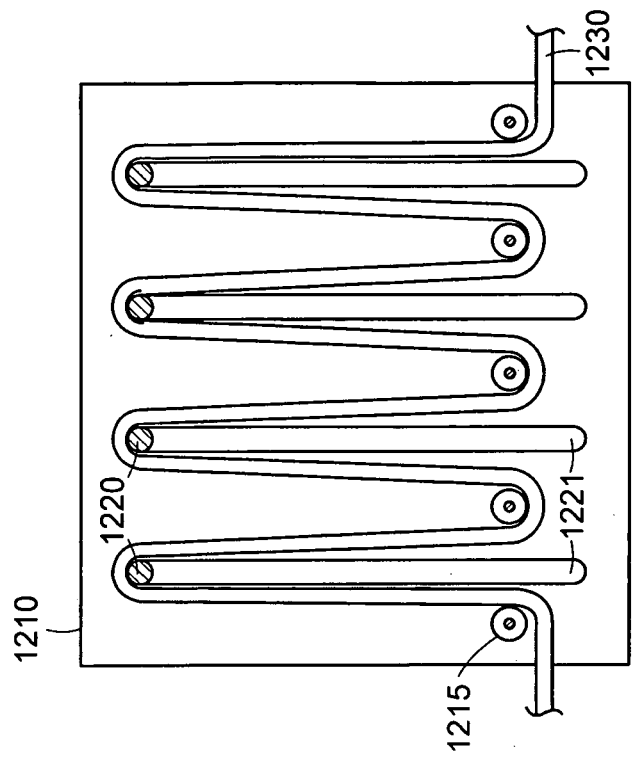
FIGS. 8A and 8B schematically show a tube length adjuster with variable internal length, in accordance with an embodiment of the present invention.
Figure 8B:
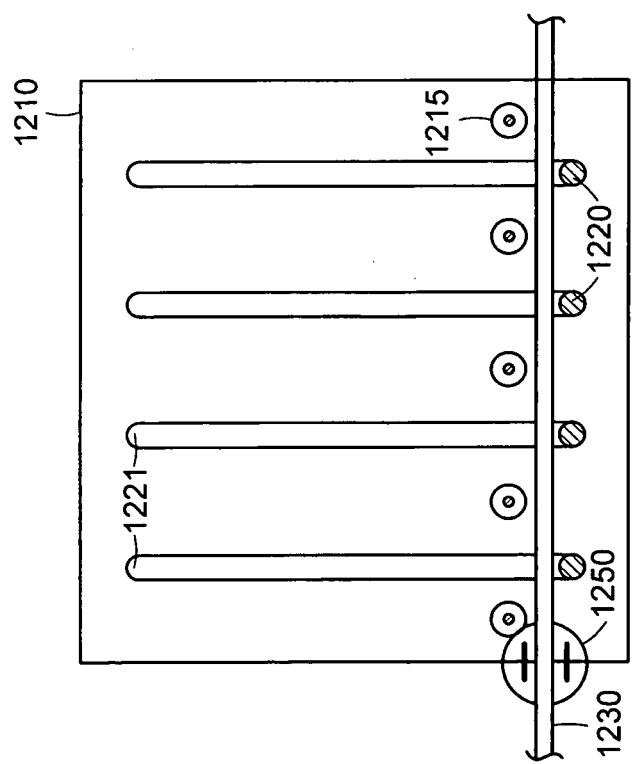

FIGS. 8A and 8B show another example of tube length adjuster with variable internal length. In FIG. 8A, an internal view of the adjuster where a plurality of sliders 1220, each slider 1220 having a track 1221 in the casing, is depicted along with a set of stationary guides 1215. Although, the housing of the adjuster is depicted as flat, a person of skill in the art would recognize that the housing may be any shape or form to make it compact and portable. As shown in FIG. 8A, tubing 1230 may be loaded into the casing, squeezed between the guides 1215 and sliders 1220. The guides 1215 may include a roller annularly positioned around the guide 1215 to enhance tubing motion around the post 1215. Likewise, the sliders 1220 may also include an annular roller. The tubing 1230 may be removably attached to the case 1250. Now referring to FIG. 8B, the sliders 1220 may be moved within the their respective tracks 1221, to alter the internal path and thus length of tubing present within the casing. The sliders 1220 may be moved independently of each other (as shown in FIG. 8B), or be coupled in some manner to move simultaneously. A lock for at least one of the sliders 1220 may also be utilized to fix the length of tubing within the case.

Figure 9A:
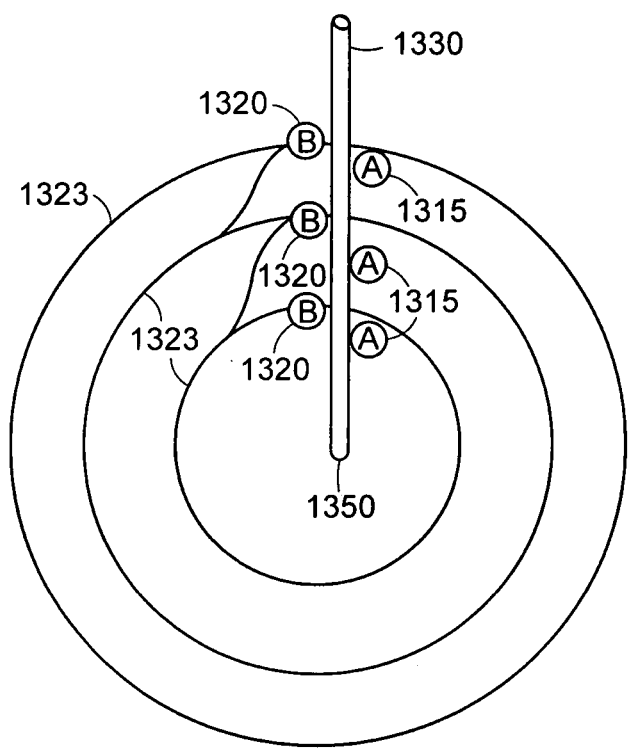
FIGS. 9A-9C schematically show a tube length adjuster having tracks of sliders configured to move in a circular path, in accordance with an embodiment of the present invention.
Figure 9B:
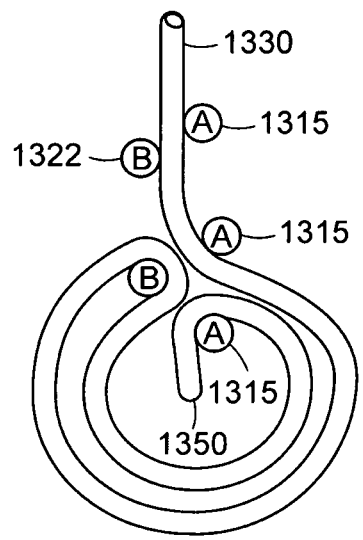
Figure 9C:
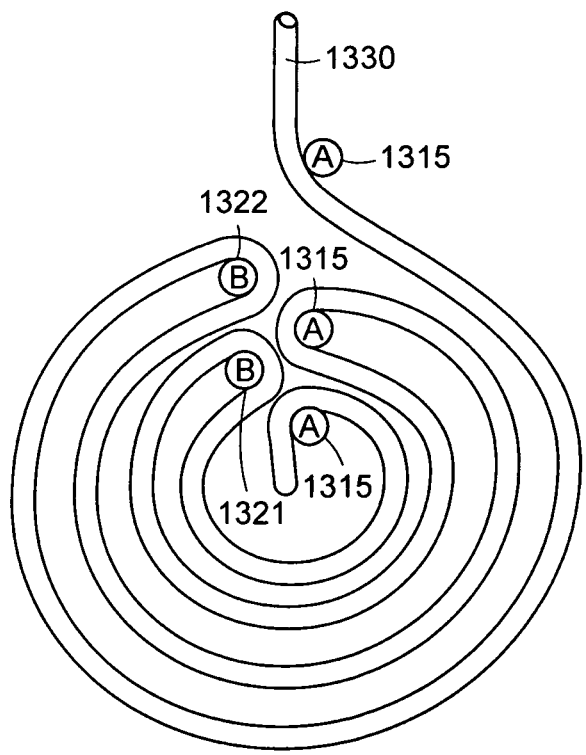

FIGS. 9A-9C depict an adjuster in accord with an embodiment of the invention. The adjuster in FIGS. 9A-9C is operational similar to the adjuster in FIGS. 8A and 8B, except that the tracks 1323 of the sliders 1320 in FIGS. 9A-9C are configured to move in a circular path, in any direction, as opposed to the straight line path of FIGS. 8A and 8B. As depicted in FIG. 9A, tubing 1330 may be mounted between the sliders 1320 and guides 1315 through an opening 1350 in the adjuster. The opening 1350 may also act as a friction structure to allow removable attachment of the tubing 1330 at that location. FIG. 9B depicts the configuration of the tubing 1330 after slider 1321 has been moved clockwise through its track. FIG. 9C depicts the configuration of the tubing 1330 after sliders 1321 and 1322 have been moved clockwise through their tracks.

Figure 10A:
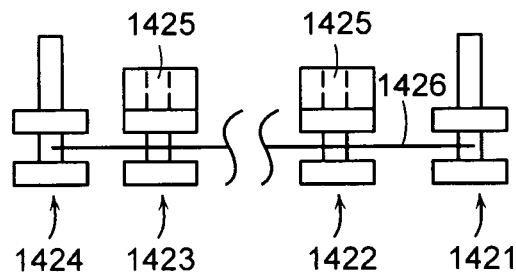
FIGS. 10A-10C schematically show a tube length adjuster with a variable internal path, in accordance with an embodiment of the present invention.
Figure 10B:
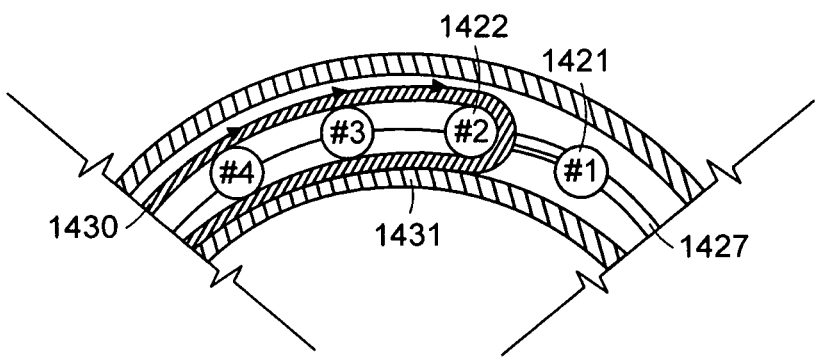
Figure 10C:
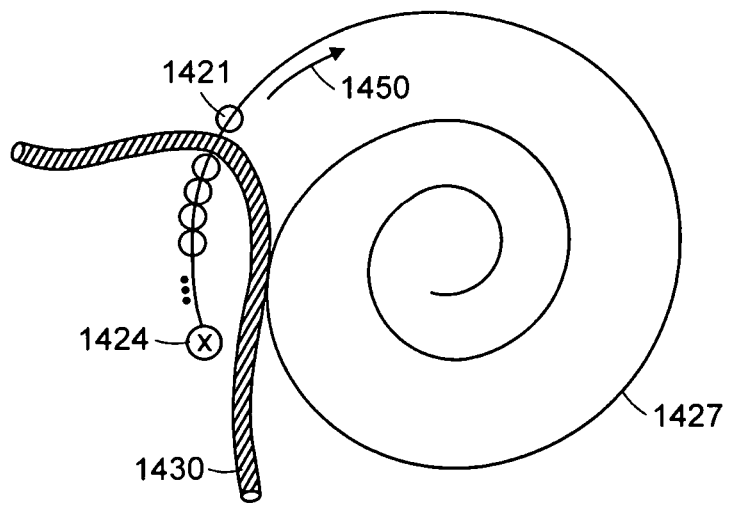

FIGS. 10A-10C depict components of another adjuster with a variable internal path for tubing in accord with an embodiment of the invention. A set of sliders 1421, 1422, 1423, 1424 are arranged in series to travel in a train along a track 1427 as shown in FIGS. 10A and 10B. The sliders 1421, 1422, 1423, 1424 may be coupled together such that the movement of one slider induces movement in the other sliders. As shown in FIG. 10A, the sliders are flexibly coupled with a flexible tether 1426. A person skilled in the art will recognize other mechanisms for achieving the coupling. Still referring to FIG. 10A, each slider 1421, 1422, 1423, 1424 may utilize a roller 1425 to aid movement of the tubing along its surface. Now referring to FIG. 10B, tubing 1430 may be inserted around one slider 1422 adjacent to an end of the slider train 1421. As shown in FIG. 10C, the slider at the head of the train 1421 may be moved along a track 1427 in direction 1450 to increase the length of tubing stored within the adjuster. One possible track configuration is a spiral as shown in FIG. 10C. Alternatively, any track configuration may be used to store the tubing. Preferably, the track is configured to provide a compact and efficient storage in the available compartment. As shown in FIG. 10C, the sliders 1421, 1422, 1423, 1424 may be moved by moving the head slider 1421, by use of a turnable handle coupled to the slider train, or the use of an elastic member that is biased in a particular direction to attain its equilibrium position. The track 1427 and sliders 1421, 1422, 1423, 1424 may be configured such that tubing 1430 has a tendency to adhere to one side wall 1431 of the adjuster, thus fixing the tube 1430. The tube 1430 may be released from the adjuster by either pulling on the free end of the tubing or moving the opposite end of the slider train 1424 in the opposite direction of 1450, to free tubing.

As documented by the examples shown in FIGS. 7-10, one skilled in the art will readily recognize that embodiments of the invention may utilize any number of sliders, designed to travel in any number of tracks in any given orientation in order to create path lengths within a case to adjust the unexposed length of tubing. The guides used in such embodiments of the invention may have a variety of shapes and sizes, and one or more may be utilized with various embodiments. Movement of the sliders may be by user manipulation of individual, or a set of coupled, sliders, use of a mechanical crank coupled to one or more sliders, or the use of an elastic member with a tendency to bias movement of the sliders in a direction to lengthen the variable internal path. In the latter case, the unstored length of tubing is fixed when the tension in the tubing is balanced by the force induced by the elastic member.

Figure 11A:
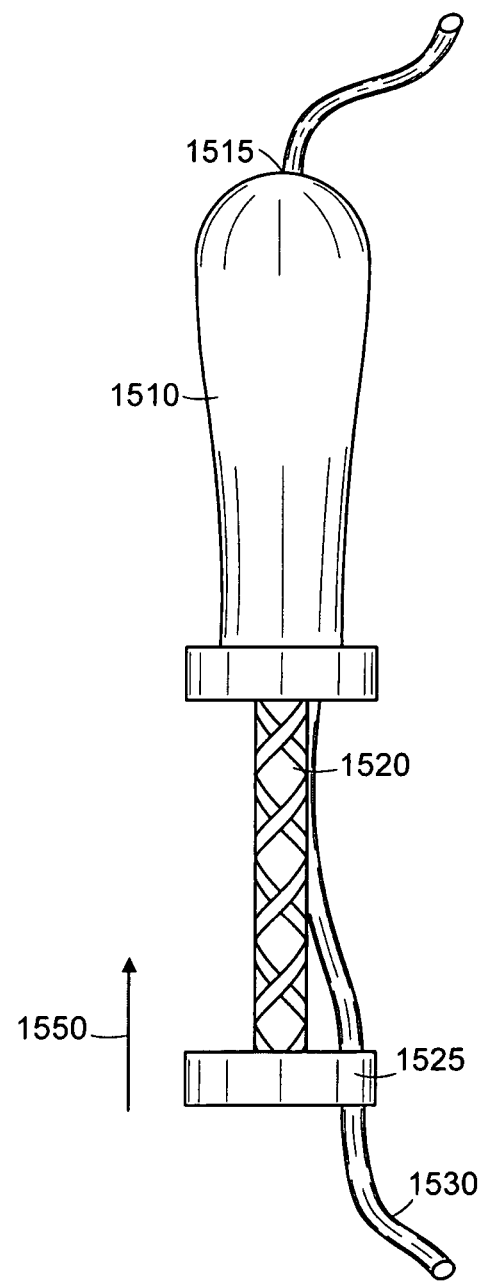
FIGS. 11A-11C schematically show a tube length adjuster having a rotatable shaft and handle, in accordance with an embodiment of the present invention in use.
Figure 11C:
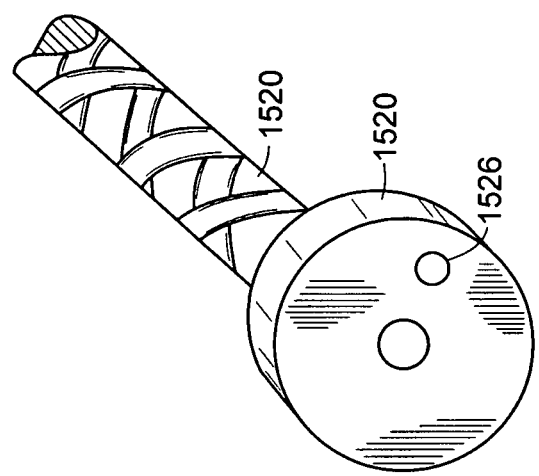
Figure 11B:
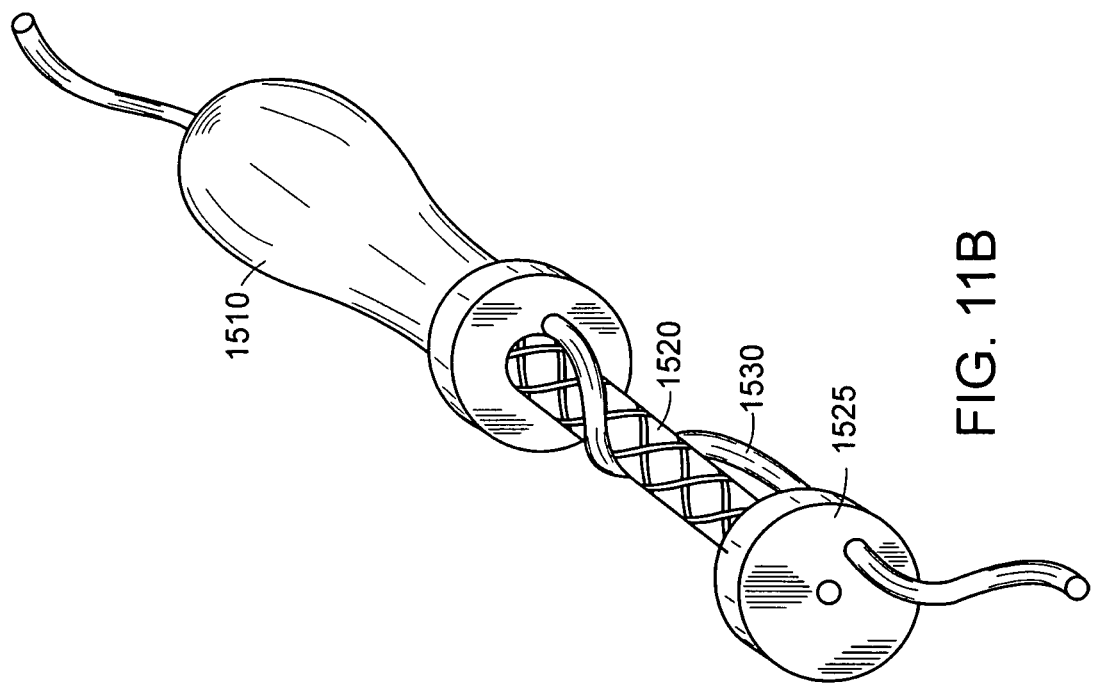

An alternate embodiment of the invention is shown by the tube length adjuster in FIGS. 11A-11C. As shown in FIG. 11A, the adjuster includes a rotatable shaft 1520 and a handle 1510. The rotatable shaft 1520 includes a tube guide 1525, as shown in FIG. 11C, which is capable of winding tubing 1530 around the shaft 1520 while it rotates. The handle 1510 includes an opening 1515 for allowing tube 1530 to be threaded out of the handle 1510, a structure for removably attaching the tube (such as a friction structure), and a hollow region with a spiral notch. The spiral notch has an axis parallel to the axis of the shaft 1520 and is in contact with the rotatable shaft 1520. By moving the handle 1510 in a direction 1550 parallel to the direction of the axis of the shaft 1520, the shaft 1520 rotates and tubing 1530 is wound around the shaft and stored. A lock is optionally utilized to lock the handle position and fix the length of tubing not wound around the shaft. In an alternate embodiment, the spiral notch may be ratcheted to allow controlled wind-up of tubing 1530 without a lock mechanism.

Although various exemplary embodiments of the invention, and examples thereof, have been disclosed, those skilled in the art will recognize that various changes and modifications can be made which will achieve some of the advantages of the invention without departing from the true scope of the invention. Furthermore, attachment features such as straps including fasteners, velcro, buttons, snaps, clips and other attachment means may be included with the present invention to facilitate the attachment or placement of the present invention on the user.

What is claimed is:

1. A method of adjusting an unstored length of tube to transfer a fluid into a living body, the method comprising the steps of:
   providing a tube capable of connecting a fluid source to the living body;
   providing a user-wearable tube length adjuster, the adjuster including a storage module having an inner hub sandwiched by a first exterior disc and a second exterior disc, the first exterior disc and the second exterior disc having opposed exterior surfaces formed on sides of the first and second exterior discs opposite the hub, the exterior surfaces extending over substantially the entire side of the first exterior disc and the entire side of the second exterior disc opposite the hub, at least one exterior surface having at least a first trough-shaped notch and a second trough-shaped notch formed therein, the first trough-shaped notch and the second trough-shaped notch formed next to one another in the exterior surface and traversing the entire exterior surface by extending from a first point on a circumference of the respective exterior disc to a second point on the circumference of the respective exterior disc, the first trough-shaped notch configured to contain at least a first portion of a length of tube and the second trough-shaped notch configured to contain at least a second portion of the length of tube, the storage module configured wherein the tube may be wrapped about the hub between the first exterior disc and the second exterior disc;
   removably attaching the tube to the adjuster by wrapping the tube about the hub and by accommodating the first portion of the length of tube within the first trough-shaped notch and the second portion of the length of tube within the second trough-shaped notch; and
   storing a portion of the tube on the storage module to adjust the unstored length of tube.

2. A method according to claim 1 further comprising the step of fixing the unwrapped length of the tube onto a fastening device for maintaining the length of the tube about the storage module.

3. A method according to claim 1, wherein the fluid source includes insulin.

4. A method according to claim 1, wherein the storage module includes at least one fastening device, and storing the portion of the tube includes fastening the tube on the at least one fastening device.

5. A method according to claim 1, wherein removably attaching the tube to the adjuster includes removably attaching the tube to the storage module.

6. A method according to claim 1, wherein storing a portion of the tube includes rotating the tube about the storage module.

7. A tube length adjuster comprising:
   a storage module having an inner hub sandwiched by a first exterior disc and a second exterior disc, the first exterior disc and the second exterior disc having opposed exterior surfaces formed on sides of the first and second exterior discs opposite the hub, the exterior surfaces extending over substantially the entire side of the first exterior disc and the entire side of the second exterior disc opposite the hub, at least one exterior surface having at least a first trough-shaped notch and a second trough-shaped notch formed therein, the first trough-shaped notch and the second trough-shaped notch formed next to one another in the exterior surface and traversing the entire exterior surface by extending from a first point on a circumference of the respective exterior disc to a second point on the circumference of the respective exterior disc, the first trough-shaped notch configured to contain at least a first portion of a length of tube configured to carry fluids and the second trough-shaped notch configured to contain at least a second portion of the length of tube, the storage module configured to allow at least a portion of the length of tube to be wrapped about the hub between the first exterior disc and the second exterior disc and at least a first portion of the length of tube to be contained within the first trough-shaped notch and at least a second portion of the length of tube to be contained within the second trough-shaped notch; and
   at least one fastening device for maintaining the first portion of the length of tube contained in the first trough-shaped notch and the second portion of the length of tube contained in the second trough-shaped notch;

wherein wrapping the tube about the hub shortens the tube and unwrapping the tube from the hub lengthens the tube.

8. A tube length adjuster according to claim 7, wherein the storage module includes a plurality of fastening devices, each fastening device capable of maintaining the length of tube.

9. A tube length adjuster according to claim 8, wherein the fastening devices are frictional surfaces.

10. A tube length adjuster according to claim 7, wherein the at least one fastening device is a fastener wherein the fastener wraps around the length of tube contained in the at least one notch whereby the fastener maintains the length of tube wrapped about the storage module surface.

11. A tube length adjuster according to claim 7 wherein the at least one fastening device further comprising a friction structure.

* * * * *